United States Patent [19]
Newell

[11] Patent Number: 5,284,063
[45] Date of Patent: Feb. 8, 1994

[54] CREEP TEST COUPON FOR METAL MATRIX COMPOSITES

[75] Inventor: Kenneth J. Newell, Redondo Beach, Calif.

[73] Assignee: Rockwell International Corporation, Seal Beach, Calif.

[21] Appl. No.: 664,196

[22] Filed: Mar. 4, 1991

[51] Int. Cl.$^5$ .............................................. G01N 3/08
[52] U.S. Cl. ......................................... 73/822; 73/826
[58] Field of Search .......................... 73/818, 822, 826; 428/137

[56] References Cited

U.S. PATENT DOCUMENTS

| | | | |
|---|---|---|---|
| 2,831,342 | 4/1958 | Adler et al. | 73/826 |
| 4,378,702 | 4/1983 | Meier | 73/826 |
| 4,895,750 | 1/1990 | Pratt | 73/1 R |
| 5,036,577 | 8/1991 | Swank | 73/826 |
| 5,083,465 | 1/1992 | Myers | 73/826 |

FOREIGN PATENT DOCUMENTS

| | | | |
|---|---|---|---|
| 800796 | 2/1981 | U.S.S.R. | 73/826 |
| 1224658 | 4/1986 | U.S.S.R. | 73/826 |

Primary Examiner—Robert Raevis
Assistant Examiner—Nashimiya Ashraf
Attorney, Agent, or Firm—Terrell P. Lewis; Charles T. Silberberg

[57] ABSTRACT

A test coupon for metal matrix composites is provided with means for structurally isolating the reinforcing fibers in the gage section from the reinforcing fibers in the clamped end regions of the coupon, when the latter is subjected to creep testing, so that the results of creep testing can be more accurately indicative of the creep properties associated with the fiber-reinforced metal matrix composite material in the coupon gage section. More particularly, the test coupon of the invention is provided with a plurality of slots or cut-out regions disposed in a section located between the clamped end regions and the centrally located gage section. The plurality of slots, which can be provided in longitudinally and/or laterally staggered arrays, effectively causes structural isolation of the reinforcing fibers in the gage section from the clamped reinforcing fibers located in the end regions of the coupon.

13 Claims, 4 Drawing Sheets

CREEP TEST COUPON FOR METAL MATRIX COMPOSITES

STATEMENT OF GOVERNMENT INTEREST

This invention was made with Government support under Contract No. F33657-86-C-2127 awarded by the U.S. Air Force. The Government has certain rights in this invention.

BACKGROUND OF THE INVENTION

1. Field of the Invention

The present invention relates to test coupons for determining creep characteristics for metal matrix composite structures, and more particularly to methods for forming and using such coupons and to configurations of the coupon itself.

2. Background of the Invention

The use of creep test coupons to determine structural properties and behavioral characteristics is not new. For many years, such coupons have been provided as samples of monolithic materials requiring investigation. Testing of the samples has been accomplished by subjecting them to compressive and/or tensile forces in appropriate testing apparatus, thereby making it possible to obtain data indicative of the character of materials in question.

Recently, new composite materials known as "metal matrix composites" (MMC's) have been developed for use in the aerospace industry, and there has arisen a great and urgent need for investigation of the properties of these materials as well.

In order to accomplish this task, the industry typically has performed creep and other types of material characteristic testing using a coupon of substantially rectangular shape having simple straight, parallel sides (see FIG. 1) or a coupon formed in a dog-bone shape (see FIG. 2).

To date, the latter configuration has been widely accepted as the industry standard. FIG. 3 illustrates this configuration of coupon when used with fiber-reinforced metal matrix materials. As is well known, the reinforcing fibers are embedded in the metal matrix material. The plurality of fibers include one or more layers of fiber sets, where in each layer the fibers are disposed at a predetermined angle (between 0° and 90°) relative to the longitudinal axis Z—Z of the coupon. Each set of angularly oriented fibers typically extends along a portion (if not all) of the length of the coupon. Those sets of fibers having no angular orientation relative to the coupon longitudinal axis (i.e., zero (0) degrees orientation) typically span the length of the coupon from one end region to the opposite end region.

Exemplary of such an angular arrangement of reinforcing fibers in a test coupon are the fiber sets 310, 320 and 330 shown in FIG. 3. Fiber set 310 is oriented at +45° relative to the longitudinal axis Z—Z of the coupon, fiber set 330 is oriented at −45° relative to the longitudinal axis, and fiber set 320 is positioned at an angular orientation of approximately zero degrees relative to the longitudinal axis Z—Z. The FIG. 3 representation of fiber sets does not purport to identify upper, middle and lower sets of fibers, but rather only is illustrative of three possible angular orientations of the fiber sets. Holes 302, 304 located in opposite end regions of the coupon serve as alignment means for facilitating attachment of the coupon in the testing fixture. As stated above, the three fiber sets depicted in FIG. 3 are merely intended to serve as illustrative examples of the infinite number of angular orientations possible. The number of fiber sets in any given test coupon, the different angular orientations of these fiber sets, and the relative placement of these fiber sets one above the other are all considered to be design considerations which depend on which, and to what degree of magnitude, strength-of-material characteristics are being developed.

Testing of coupons is typically accomplished by first securing opposite ends of the coupons in fixture clamps, and then subjecting the coupon to tensile or compressive forces, as the case warrants, to obtain the creep (or stress or strain) characteristics of the material involved.

One of the most disturbing problems attendant the use of the known fiber-reinforced MMC coupon configurations is that, after the coupon is clamped and the testing takes place, the test results produce creep curves which suggest that the section of fiber-reinforced metal matrix compound material located between the clamped end regions (i.e., in the gage section) is just as strong as the fibers disposed within the metal matrix compound material. In other words, an accurate reading of the test results with a high level of confidence cannot be obtained in carrying out standard testing procedures with the presently known test coupon configurations.

A situation in which the fiber-reinforced metal matrix compound material of the gage section would be expected to be as strong as the fibers in the MMC material would be where the coupon was perfectly fastened at both end regions and subjected only to a pure tension load. However, it would be presumptuous to believe that perfect loading or perfect clamping of the coupon could be attainable in practice. Indeed, it is believed that, in using the conventional coupon configurations and currently known procedures of clamping and testing coupons fabricated from fiber-reinforced metal matrix compound materials, creep strain (known to be recoverable in a monolithic material) would be trapped.

OBJECTS AND SUMMARY OF THE INVENTION

It is therefore an object of the present invention to provide a novel coupon configuration which will permit a more accurate determination of structural properties of matrix metal composite (MMC) materials, while at the same time overcoming all the deficiencies and disadvantages of the known coupon configurations for such MMC materials.

Another object of the present invention is to provide a new design for fiber reinforced MMC material test coupons in which the fiber-reinforced material located in the section of the coupon between the clamped end regions (i.e., the gage or measurement section) is physically isolated from the fibers at the clamped end regions.

Still another object of the invention is to provide a test coupon configuration which is envisioned as the next industry standard for tests on fiber-reinforced materials.

Yet another object of the invention is to provide a novel method for fabricating test coupons manufactured from fiber-reinforced materials whereby creep behavior of the materials can be accurately determined.

These and other objects are accomplished through the application of the surprising results discovered by the present inventor that the structural effect of reinforcing fibers in the gage section of a test coupon subjected to creep testing can be isolated from the reinforcing fibers located in the clamped end regions of the coupon, and therefore the results of creep testing will be more accurately indicative of the creep properties associated with the fiber-reinforced metal matrix composite material in the centrally located gage section.

More particularly, in accordance with the principles of the present invention, these objects are accomplished by the fabrication of a test coupon having slots or cutout regions disposed in a section located between the clamped end regions and the centrally located measurement section. The test coupon has any shape determined to be most appropriate for achieving the desired results, e.g., rectangular, square, circular, elliptical, etc. That which is most important is to provide a perimeter of isolating slots or perforations about the centrally located measurement section of the test coupon.

DETAILED DESCRIPTION OF THE INVENTION

Figure 1:
FIGS. 1 and 2 illustrate two configurations of test coupons typically used for determining structural properties of fiber-reinforced matrix materials.
Figure 2:
Figure 3:
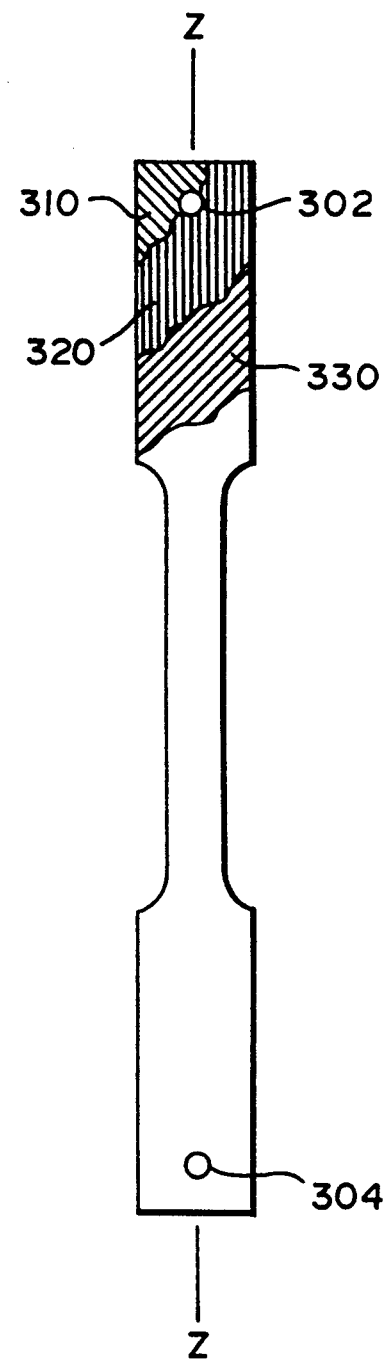
FIG. 3 depicts several exemplary angular orientations of fiber sets found in a fiber-reinforced MMC test coupon configuration typically used by the testing industry.
Figure 4:
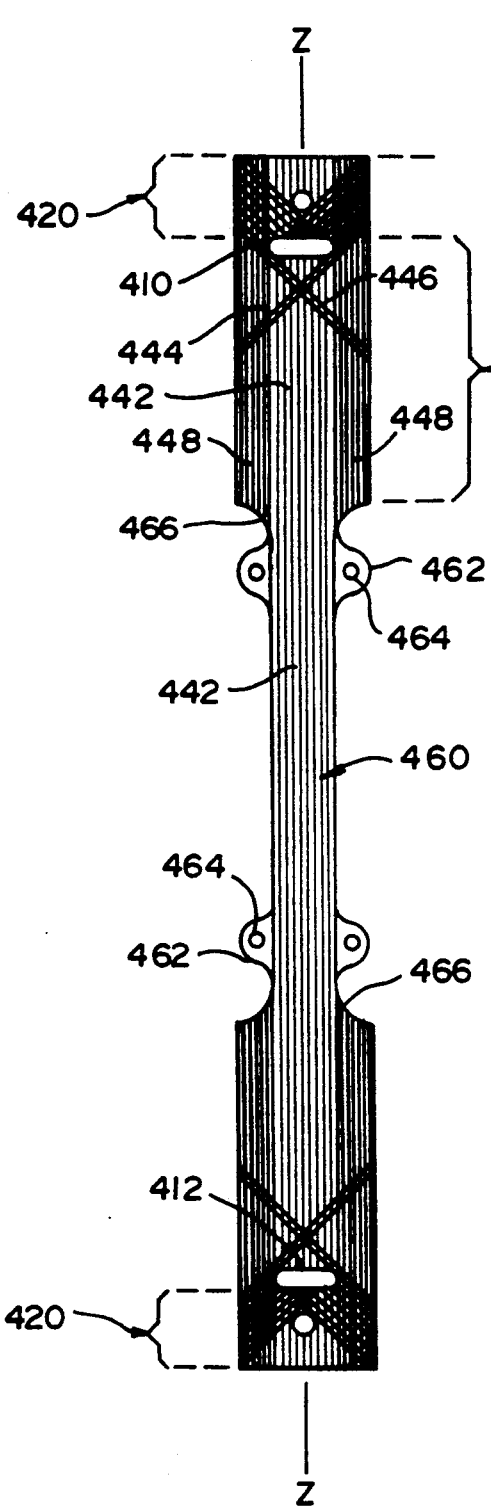
FIG. 4 illustrates a first configuration of the fiber reinforced test coupon contemplated by the present invention depicting an orientation of fiber sets similar to that shown in FIG. 3 on the test coupon and the means associated with the test coupon for isolating the fiber-containing gage section from the clamped end regions.
Figure 5:
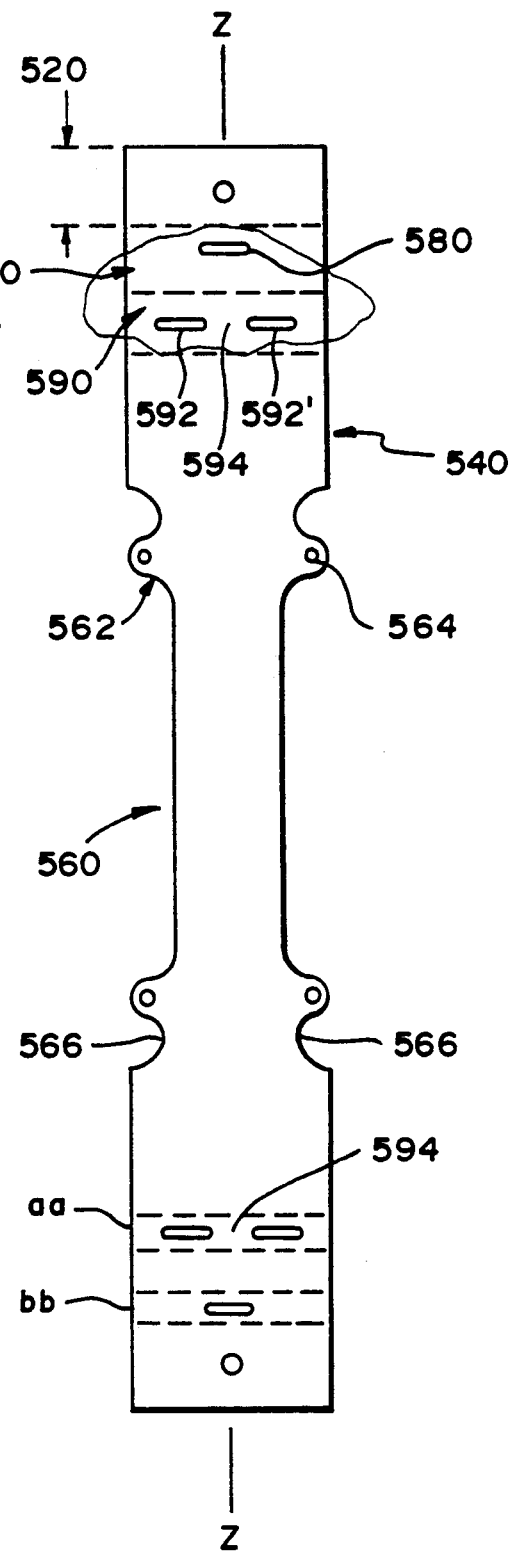
FIG. 5 illustrates a second configuration of the fiber reinforced test coupon contemplated by the present invention depicting an orientation of fiber sets similar to that shown in FIG. 3 on the test coupon and the means associated with the test coupon for isolating the fiber-containing gage section from the clamped end regions.
Figure 6:
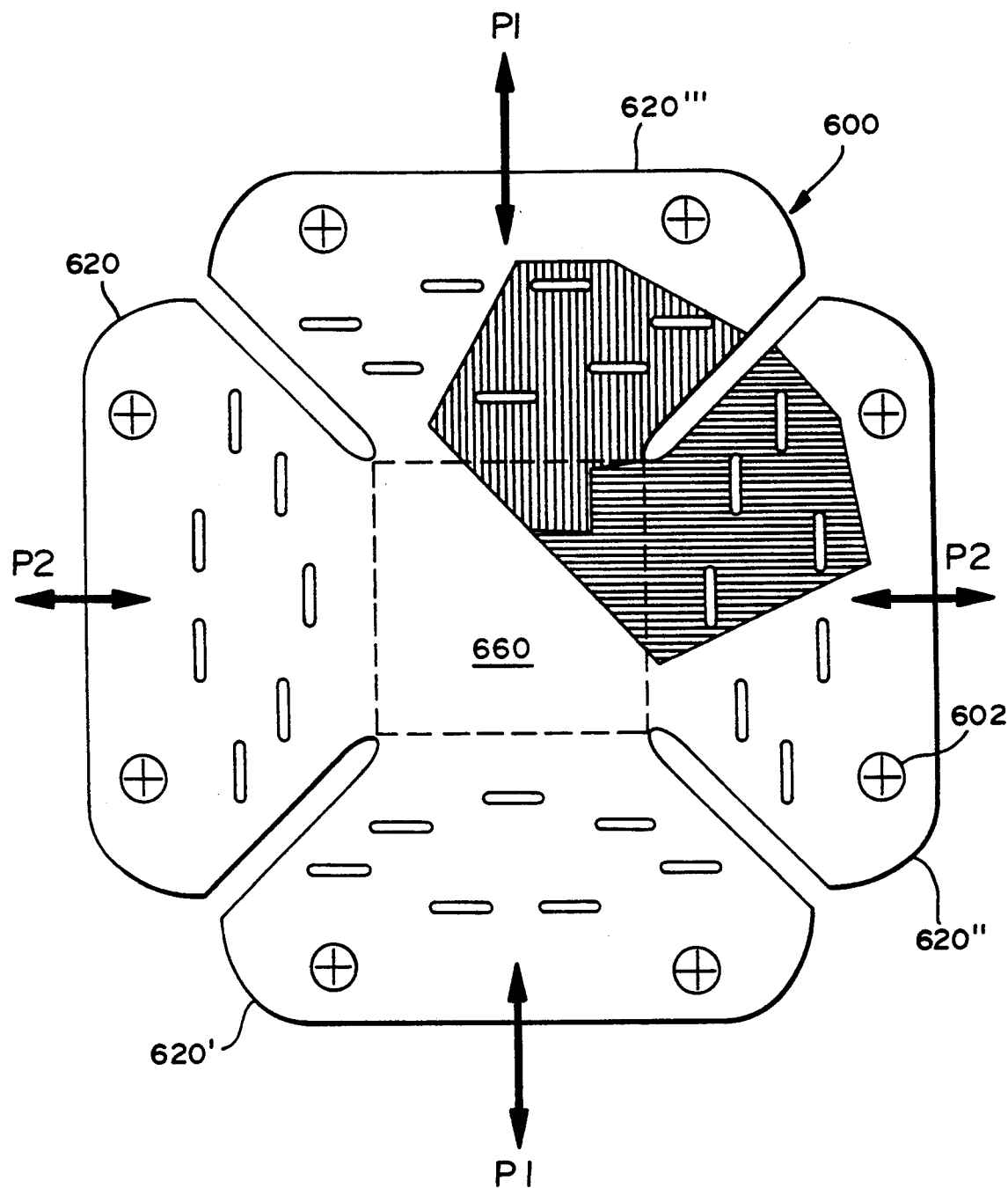
FIG. 6 illustrates a third configuration of the fiber reinforced test coupon contemplated by the present invention depicting means associated with the test coupon for isolating the fiber-containing gage section from the clamped end regions.

Referring now to FIGS. 4–6, wherein identical or similar references numerals represent identical or similar structural components, there are shown three novel configurations of a test coupon embraced by the present invention.

In the configuration of FIG. 4, coupon 400 includes three primary portions; a first set of clamp portions 420, 420, a second gage portion 460, and a third set of medial portions 440 interposed between each clamp portion and the gage portion. The gage portion is bounded on opposite sides by a pair of circular protruberant regions 462 each of which is provided with an aperture 464 by means of which an extensometer or similar device can be attached to measure relative elongation of the gage portion. Stress relief areas may optionally be provided (note areas 466) to separate the protruberant regions 462 from the medial portions 440. It is to be understood that the regions 462 and apertures 464, as well as the stress relief areas might also be provided on any of the test coupons disclosed herein and contemplated by the present invention.

Each of the medial portions 440 includes a slot 410, 412 with an elongated opening which extends laterally across the coupon in the direction of the external face of the width. Each slot is configured such that the regions of metal matrix compound material in the medial portion located between the edges of the coupon and the edges of the slot together have a linear lateral dimension greater than the lineal lateral dimension of the slot.

The effect of providing the slots 410 and 412 is to isolate the fibers of the clamp and medial regions from the fibers of the gage portion. Looking at FIG. 4, it can be seen that the zero degree fibers 442 and off-axis fiber sets 444 and 446 in the clamp and medial portions are interrupted by the slots 410 and 412, and consequently neither extend into the gage portion nor impact on the fiber set 442 contained in the gage portion. Indeed, the fiber set 442 in the gage portion has been effectively structurally isolated from the fiber sets 442, 444, 446 and 448 in the clamp portion of the coupon. p The "slotted" design of test coupon embraced by the present invention permits load transference to the gage portion through the metal matrix compound and the off axis fiber sets (i.e., note fiber sets 444 and 446 in FIG. 4) which are not affected by the slots. Further, as a result of this construction, the gage portion will carry a higher stress level due to the lateral dimension being smaller across the gage section than the sum of the lateral dimensions of material at the location of the slot(s).

Referring now to FIG. 5, wherein the same or similar reference numerals represent the same or similar structural features, there is shown a second configuration for the test coupon with which this application is concerned. This second configuration is substantially identical to the configuration of FIG. 4, with the exception of the array AA of slots extending across the medial portions. The slots shown extend in a direction normal to the longitudinal axis Z—Z of the coupon. Each array of slots includes two "regions" 580, 590 of slots. It is contemplated that region 580 would include at least one slot (only one slot is shown in this Figure), and region 590 would include at least two slots 592, 592'. The slots in each of the two regions extend in the direction normal to the longitudinal axis Z—Z such that two "virtual rows" aa, bb are defined (see bottom of FIG. 5). These "virtual rows" are spaced apart and are effectively parallel to one another. The slots in the two "virtual rows" are staggered in the direction perpendicular to the Z—Z axis, with a slot in one "virtual row" being disposed longitudinally above or below a region 594 of metal matrix compound material surrounding or located adjacent to the adjacent end portions of the slots 592, 592' in the other "virtual row". It is understood that either of the one or the other "virtual rows" may contain one or more slots, but the concept which applicant wishes to convey is that the slots in one "virtual row" are offset in a direction perpendicular to the longitudinal axis from the slot(s) in the other "virtual row". Of course, the invention also contemplates the provision of more than two "virtual rows" of slots located at predetermined positions along the longitudinal axis of the coupon.

A third configuration of test coupon 600 is disclosed in FIG. 6 where, once again, the same or similar reference numerals represent the same or similar structural features. Here the coupon has a substantially square gage portion 660 and is secured to a test fixture via four clamp portions 620, 620', 620'', 620''', each clamp portion being disposed adjacent a respective one of the edges of the gage portion. Due to the substantial area of the clamp portions which must be secured in the test fixture, and the fact that, in this coupon configuration, each of the clamp portions are structurally independent from any one of the other clamp portions, a plurality of alignment holes 602 are provided to facilitate securing the coupon in the fixture. In contrast to the coupon configuration of FIG. 5, the test coupon of this embodiment is designed to be subjected to loads along two axes (i.e., "biaxially") either alternately or concurrently, and includes several "virtual rows" of slots, the emphasis being on making sure that the gage portion be as completely isolated from the reinforcing fibers provided in the clamp portions of the coupon as possible, while insuring that the sum of the lateral dimensions of material between slots be greater than the lateral dimension across the gage portion.

It is contemplated that the number of "virtual rows" of slots could be chosen according to the needs of the situation at hand and the requirements of the tests being performed. It is also contemplated that the interruptions in continuity of the MMC material provided in the test coupon could take the form of perforations or sets of perforations, with one set being staggered longitudinally and/or laterally relative to the other set(s).

In all the embodiments of the invention disclosed and described above, it is important that the totality of solid portions of the coupon (in each medial section) which separate the slots or perforations be of greater magnitude than the lateral dimension across the gage section. In other words, the sum of all the lateral dimensions of the solid sections (between the lateral edges of the slots or perforations) across the width of each medial portion must be greater than the lateral dimension across the gage section.

Figure 7:
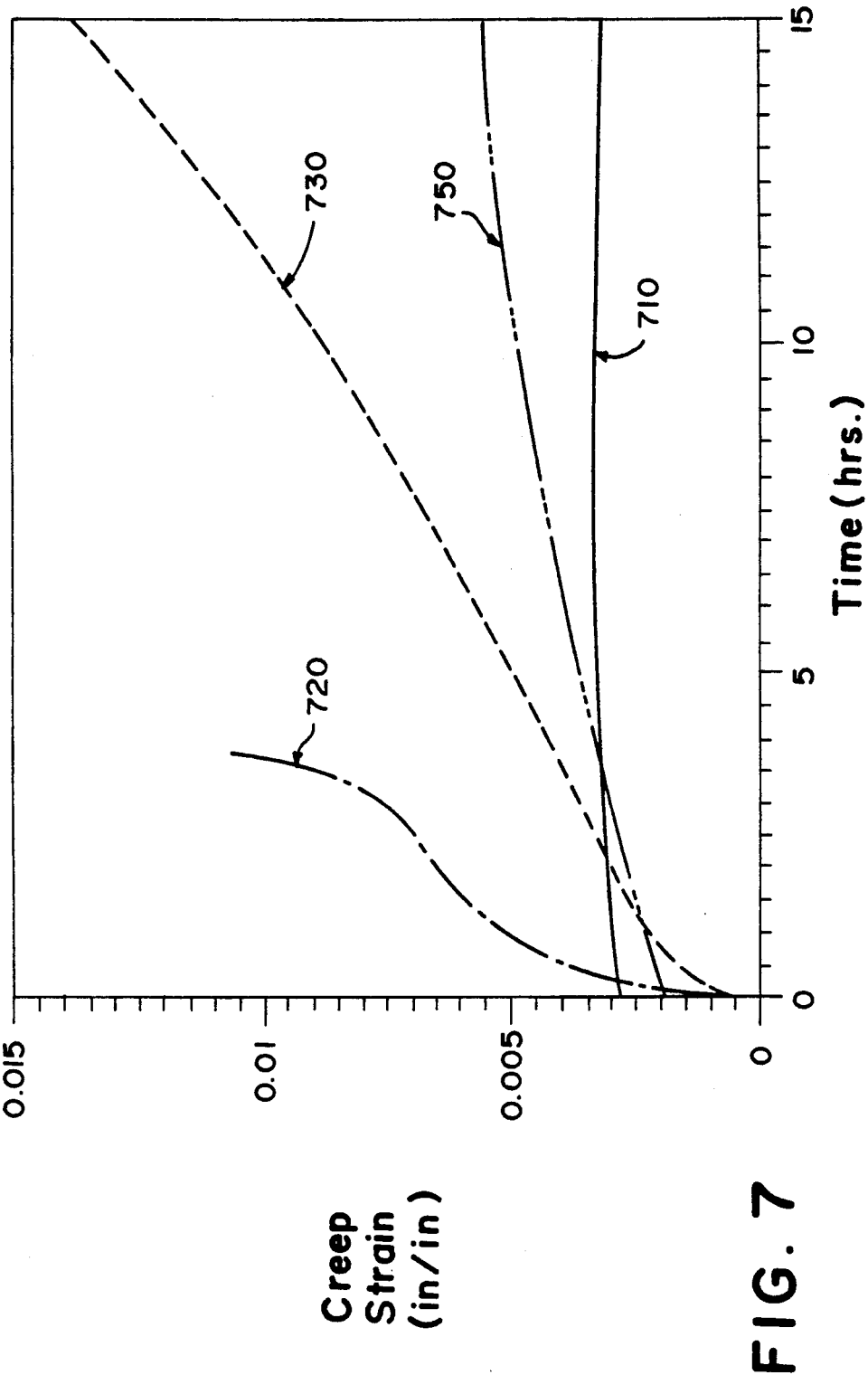
FIG. 7 is a graph showing a comparison of test results obtained from a conventional test coupon vs. a test coupon fabricated in accordance with teachings of the present invention.

FIG. 7 comparatively illustrates creep test results using actual test data for similarly configured unnotched test coupons subjected to stress-loaded conditions specified at a temperature of about 1200° F. The vertical axis represents increasing axial creep strain, while the horizontal axis represents the parameter of increasing time.

Line 710 depicts test results obtained using an unnotched fiber reinforced MMC test coupon provided with four layers of fiber arrays and subjected to a stress of approximately 38.5 ksi. In this coupon, each of the fiber arrays is aligned with the longitudinal axis of the test coupon, and the fibers are gripped at opposite ends of the coupon by the test fixture. Under application of a tensile load, the coupon behaves as if the only support for the applied load is the fibers, and as shown, curve 710 shows effectively no change in creep strain (and no material degradation) with increasing time until failure of the coupon.

Line 720 depicts test results obtained using an unslotted fiber-reinforced MMC test coupon having layers of fiber arrays arranged at 45° angles to the coupon longitudinal axis, and in a symmetrical manner (e.g., in a coupon with four layers of fiber arrays, layer 1 would be disposed at +45°, layer 2 would be disposed at −45°, layer 3 would be disposed at −45° and layer 4 would be disposed at +45°). Curve 720 shows minimal creep resistance with increasing time, with an ultimate failure. Stress level is approximately 8.82 ksi, only about 23% of the stress level applied in the situation relating to line 710.

Line 730 depicts test results obtained using an unslotted fiber-reinforced MMC test coupon having layers of fiber arrays arranged at 90° angles to the coupon longitudinal axis. Stress level applied to this coupon is approximately 4.5 ksi. In this case, the fibers in the gage section of the coupon effectively have no load-carrying function, since even though the coupon ends are gripped in the fixture (see the description above relating to the curve 710), there are no fibers in the gage section which structurally communicate with the fibers in the clamp portion. Nevertheless, in this situation, creep strain increases with increases in time since the load-bearing cross section of the test coupon gage portion is substantially diminished by the presence of the fiber arrays.

Line 750 shows the curve which is expected to be obtained using a slotted fiber-reinforced MMC test coupon of the type shown in FIGS. 4 or 5 of the present application.

What I claim is:

1. A test coupon for structural testing of fiber-reinforced metal matrix compound materials, said coupon comprising:
   a gage portion with a longitudinal axis and a predetermined length,
   a pair of end portions, each end portion including
      a clamping section at a free end thereof for clamping said end portion in a test fixture, and
      a medial section interconnecting said gage portion with said clamping section,
   said end portions being disposed opposite one another and defining therebetween said predetermined length, and
   each of said medial sections including at least one slot having an elongated opening that extends in a direction normal to said longitudinal axis along the width of the coupon.

2. The test coupon of claim 1, wherein
said at least one slot comprises at least two slots extending in said normal direction.

3. The test coupon of claim 1, wherein
said at least one slot delimits solid regions on opposite sides thereof, the sum of the lateral dimensions of said solid regions being in excess of the lateral dimension of said gage portion slot.

4. The test coupon of claim 1, wherein
said at least one slot isolates fibers in said fiber-reinforced material in said gage portion from fibers in said fiber-reinforced material in each said clamping section.

5. A fiber-reinforced metal matrix compound material coupon for conducting creep testing, said coupon comprising:
   (a) at least one set of reinforcing fibers encased in a metal matrix compound material, each set of said fibers having a predetermined angular orientation relative to a longitudinal axis of said coupon, and
   (b) at least one slot having an elongated opening that extends in a direction normal to said longitudinal axis along the width of the coupon, for structurally separating one region of each said set of fibers adapted to be subjected to tensile loading from another region of said set adapted to be gripped between jaws of a test fixture.

6. The coupon of claim 5, wherein said at least one slot comprises a plurality of slots.

7. The coupon of claim 5, wherein
said one region of said set of fibers is located in a gage section of said coupon and said another region is located in an end portion of said coupon,
said at least one slot being disposed in a portion of said coupon located between said test fixture and said gage section.

8. The coupon of claim 5, wherein
said at least one slot and a second slot are located in a plurality of regions of said coupon between said one region and each of said another region.

9. The coupon of claim 5, wherein said at least one slot comprises at least two slots.

10. The coupon of claim 6, wherein said plurality of slots comprises at least two rows of slots.

11. A method of structurally isolating a gage portion of a fiber reinforced MMC test coupon from clamp portions of the coupon, said gage portion having a longitudinal axis with a predetermined length, said clamp portions being adapted for clamping engagement within gripping jaws of a test fixture, said method comprising:
identifying a medial portion of said coupon between each of said clamp portions and said gage portion, and
providing at least one slot having an elongated opening that extends in a direction normal to said longitudinal axis in each said medial portion of said coupon, where said at least one slot extends in a direction along the width of said coupon as well as completely through the thickness of said coupon.

12. The method of claim 11, wherein the step of providing at least one slot in said medial portion of said coupon includes providing a set of slots disposed apart from one another in at least one direction such that said slots isolate reinforcing fibers in said gage portion from reinforcing fibers in said clamp portions.

13. The method of claim 11, wherein the step of providing at least one slot in said medial portion of said coupon includes cutting slot.

* * * * *